United States Patent
Branch et al.

(10) Patent No.: US 7,223,233 B2
(45) Date of Patent: May 29, 2007

(54) SYSTEMS AND TECHNIQUES FOR ILLUMINATING A SURGICAL SPACE

(75) Inventors: Charles L. Branch, Advance, NC (US); Kevin T. Foley, Germantown, TN (US); Maurice M. Smith, Cordova, TN (US); Thomas E. Roehm, III, Braden, TN (US); Harold S. Taylor, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 440 days.

(21) Appl. No.: 10/633,285

(22) Filed: Aug. 1, 2003

(65) Prior Publication Data

US 2004/0143167 A1 Jul. 22, 2004

Related U.S. Application Data

(60) Provisional application No. 60/400,563, filed on Aug. 2, 2002.

(51) Int. Cl.
*A61B 1/32* (2006.01)

(52) U.S. Cl. .................. 600/212; 600/245

(58) Field of Classification Search ........... 600/114, 600/191, 192, 199, 200, 212, 223, 245, 184, 600/204
See application file for complete search history.

(56) References Cited

U.S. PATENT DOCUMENTS

| | | | |
|---|---|---|---|
| 1,326,300 A | 12/1919 | Smit | |
| 2,235,979 A | 3/1941 | Brown | |
| 2,482,971 A * | 9/1949 | Golson | 600/184 |
| 3,075,516 A * | 1/1963 | Strauch | 600/184 |
| 3,261,350 A | 7/1966 | Wallace | |
| 3,590,232 A | 6/1971 | Sadowski | |
| 3,664,330 A | 5/1972 | Deutsch | |
| 4,173,392 A | 11/1979 | Ekinaka et al. | |
| 4,300,541 A * | 11/1981 | Burgin | 600/213 |
| 4,306,546 A * | 12/1981 | Heine et al. | 600/160 |
| 4,500,181 A | 2/1985 | Takahashi | |
| 4,562,832 A | 1/1986 | Wilder et al. | |
| 4,597,030 A | 6/1986 | Brody et al. | |
| 4,802,460 A | 2/1989 | Ohkuwa et al. | |
| 4,905,082 A | 2/1990 | Nishigaki et al. | |
| 4,907,132 A | 3/1990 | Parker | |
| 5,039,198 A | 8/1991 | VanBeek | |
| 5,165,387 A | 11/1992 | Woodson | |
| 5,334,150 A | 8/1994 | Kaali | |
| 5,353,786 A | 10/1994 | Wilk | |
| 5,354,302 A | 10/1994 | Ko | |
| 5,400,773 A | 3/1995 | Zhu et al. | |
| 5,441,041 A | 8/1995 | Sauer et al. | |

(Continued)

FOREIGN PATENT DOCUMENTS

EP 0 566 359 A2 10/1993

(Continued)

*Primary Examiner*—Cary E. O'Connor
(74) *Attorney, Agent, or Firm*—Krieg DeVault, LLP

(57) ABSTRACT

Methods and devices for illuminating a surgical space in a patient are provided. A retractor provides a portal or working path for access to a working space location in the patient. The retractor transmits and emits light from a light delivery system to illuminate the working channel and surgical space.

42 Claims, 5 Drawing Sheets

U.S. PATENT DOCUMENTS

| | | |
|---|---|---|
| 5,445,142 A | 8/1995 | Hassler, Jr. |
| 5,448,990 A | 9/1995 | De Faria-Correa |
| 5,562,696 A | 10/1996 | Nobles et al. |
| 5,584,796 A | 12/1996 | Cohen |
| 5,588,949 A | 12/1996 | Taylor et al. |
| 5,588,951 A | 12/1996 | Zhu et al. |
| 5,591,192 A | 1/1997 | Privitera et al. |
| 5,630,795 A | 5/1997 | Kuramoto et al. |
| 5,759,150 A | 6/1998 | Konou et al. |
| 5,785,648 A | 7/1998 | Min |
| 5,817,005 A | 10/1998 | Cohen |
| 5,891,013 A | 4/1999 | Thompson |
| 5,967,971 A | 10/1999 | Bolser |
| 6,129,662 A | 10/2000 | Li et al. |
| 6,139,493 A | 10/2000 | Koros et al. |
| 6,176,824 B1 | 1/2001 | Davis |
| 6,196,968 B1 | 3/2001 | Rydin et al. |
| 6,210,325 B1 | 4/2001 | Bartie et al. |
| 6,304,712 B1 | 10/2001 | Davis |
| 6,427,034 B1 | 7/2002 | Meis et al. |
| 6,551,346 B2 * | 4/2003 | Crossley ............... 607/88 |
| 2002/0080248 A1 | 6/2002 | Adair et al. |

FOREIGN PATENT DOCUMENTS

| | | |
|---|---|---|
| GB | 2 133 694 | 8/1994 |

* cited by examiner

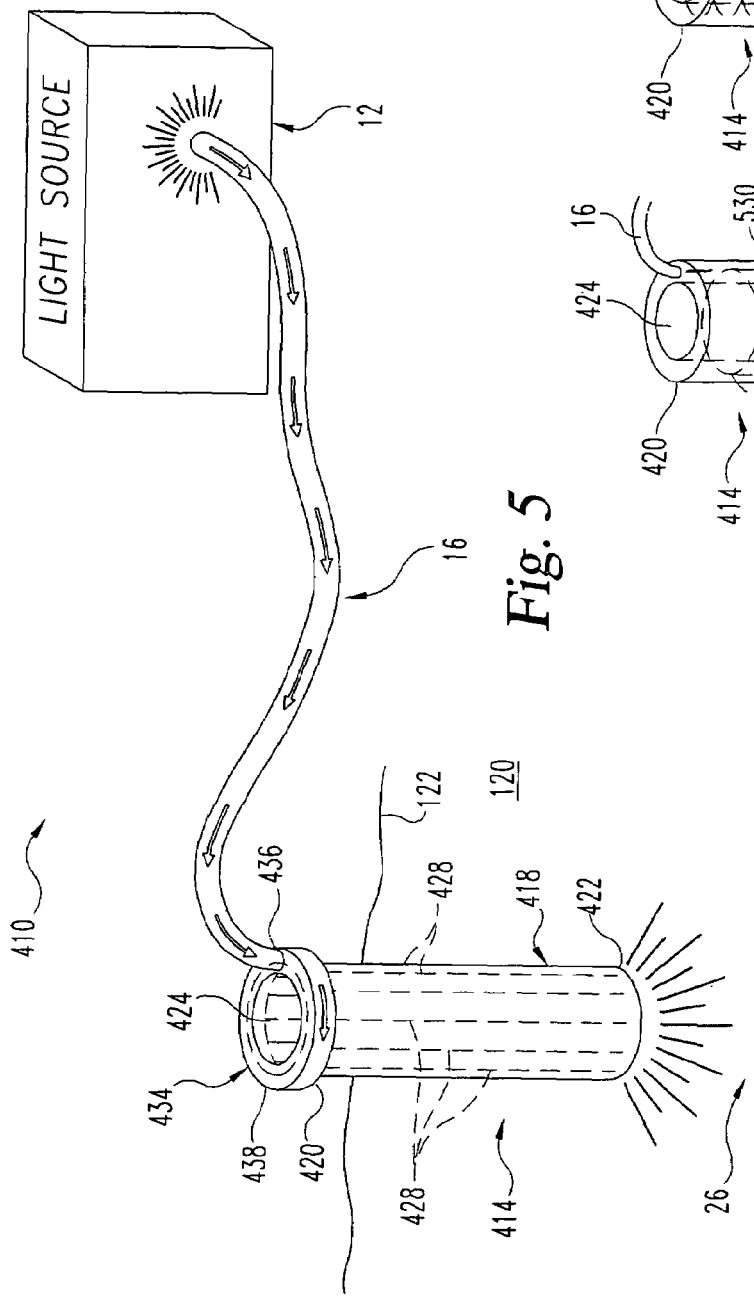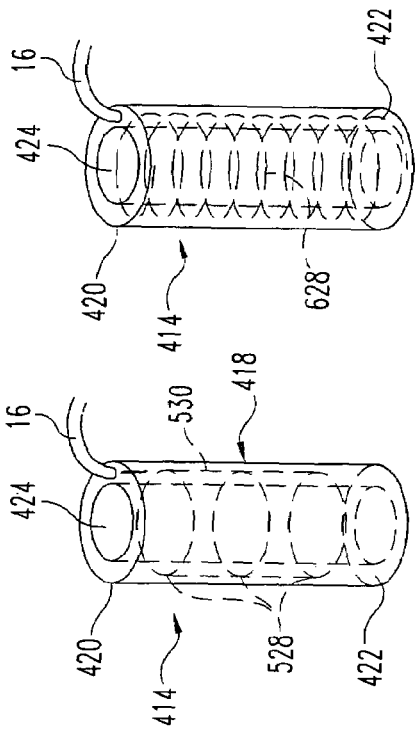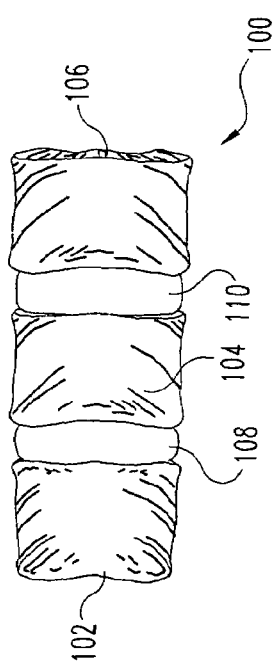

SYSTEMS AND TECHNIQUES FOR ILLUMINATING A SURGICAL SPACE

CROSS-REFERENCE TO RELATED APPLICATION

This application claims the benefit of the filing date of Provisional Application Ser. No. 60/400,563 filed on Aug. 2, 2002.

BACKGROUND

A surgical space in a patient can require illumination for the surgeon to properly perform surgical procedures in the surgical space. In minimally invasive procedures, a second portal can be provided so that a light can be positioned at the surgical space through the second portal. A light could be inserted through the same portal used by the surgeon to access the space. Also, a light could be located above the portal.

The use of such lights has several drawbacks. For example, the use of a second portal increases the invasiveness of the procedure. Positioning a light instrument through a common access portal occupies space along the working channel, making it more difficult for the surgeon to maneuver instruments in the surgical space working channel, or requiring an increase in the size of the portal and thus increasing the invasiveness of the procedure. Also, the light may be secured to the portal during the procedure, which can obstruct access to or visualization of the surgical space through the portal.

It would be desirable to provide illumination of a surgical space in a minimally invasive surgical procedure while avoiding any one or combination of the aforementioned drawbacks.

SUMMARY

According to one aspect, a system includes a retractor made from a light transmittable material coupled to a light source.

According to another aspect, a system includes a retractor made from a light transmittable material coupled to a light source. The retractor includes a light emitting surface at its distal end.

According to another aspect, a system includes a retractor made from a light transmittable material coupled to a light source. The retractor includes a light emitting surface spaced a distance from its distal end.

According to one aspect, a system includes a retractor made from a light transmittable material coupled to a light source. The retractor includes a plurality of light emitting surfaces spaced a distance from its distal end.

According to one aspect, a system includes a retractor made from a light transmittable material and can be coupled to a light source. The retractor includes a light emitting surface formed by a discontinuity in an inner surface to direct light into a working channel of the retractor.

According to one aspect, a system includes a retractor made from a light transmittable material coupled to a light source. The retractor includes at least one light transmitting element in a tubular body of the retractor radially positioned about a working channel of the retractor.

These and other aspects will also be apparent from the following description of the illustrated embodiments.

BRIEF DESCRIPTION OF THE FIGURES

FIG. 5 is a perspective view of another embodiment retractor and light delivery system.

FIG. 6 is a perspective view of another embodiment retractor for a light delivery system.

FIG. 7 is a perspective view of another embodiment retractor for use with a light delivery system.

DESCRIPTION OF THE ILLUSTRATED EMBODIMENTS

Figure 1:
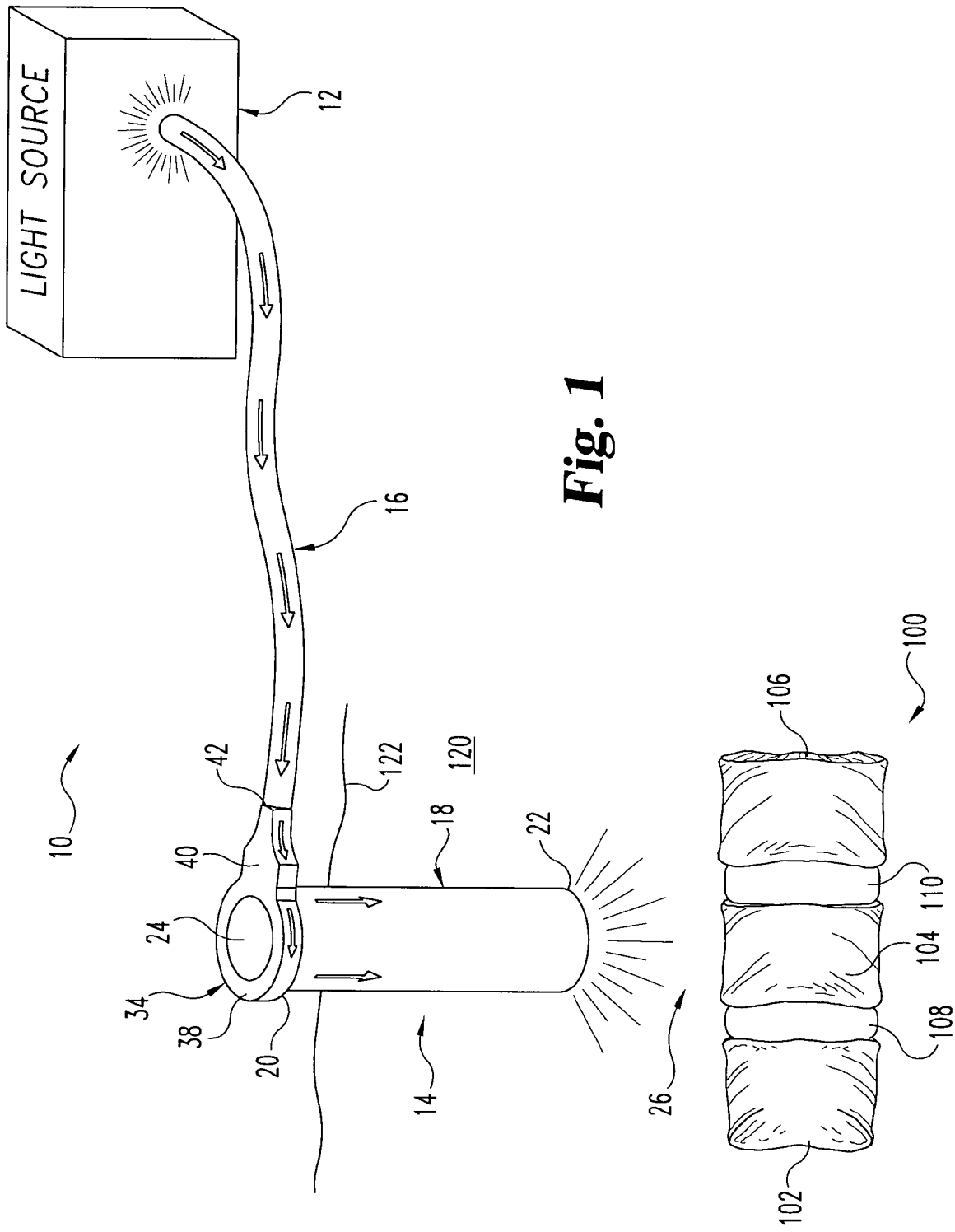
FIG. 1 is a perspective view of a retractor and light delivery system.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices and described methods, and such further applications of the principles of the invention as illustrated therein being contemplated as would normally occur to one skilled in the art to which the invention relates.

The present invention provides instruments and methods for performing surgery, such as minimally invasive surgery, in spinal applications such as laminotomy, laminectomy, foramenotomy, facetectomy, discectomy, positioning of interbody implants, positioning of intrabody implants, bone cutting and removal, tissue cutting and removal, and nerve root and tissue retraction, for example. Although the use of multiple portals is not precluded at the same vertebral level or at multiple levels, it is contemplated that a single portal within the patient can be used to perform surgical procedures. Systems and methods for providing light to the surgical space accessed by the surgeon through the portal are provided.

Referring to FIG. 1, there is shown a surgical system 10 that includes a lighting system having a light source 12 and a link 16. Light source 12 is coupled to a retractor 14 via link 16. Light source 12 provides light through link 16 to retractor 14. The light is transmitted through and dispersed at least partially about retractor 14 to illuminate the surgical space along retractor 14 and/or at the distal end of retractor 14. In the illustrated embodiment, the surgical space includes a working space 26 adjacent the spinal column segment 100. Working space 26 can include paraspinous tissue; the bony tissue of one or more of the vertebrae 102, 104, 106; the annulus tissue of disc space 108 between vertebrae 102, 104; and/or disc space 110 between vertebrae 104, 106.

Light source 12 can be any device capable of generating and/or transmitting light to link 16. Link 16 can be any one or combination of fiber optic cables, including plastic fiber optic cables, wires or other transmission device or devices capable of transferring light between light source 12 and retractor 14.

Retractor 14 includes a body 18 extending between a proximal end 20 and a distal end 22. Body 18 can define a working channel 24 therethrough extending between and opening at proximal end 20 and distal end 22. Working channel 24 can be sized to receive one or more surgical instruments therethrough to perform surgical procedures at working space 26 adjacent distal end 22 of retractor 14. Retractor 14 can be inserted over the last of one or more tissue dilators and/or guidewires sequentially positioned one around the other to gradually retract tissue 120 and skin 122 of the patient. With retractor 14 positioned through the skin and tissue, the dilators are removed to provide access to working space 26 through working channel 24. Other techniques for placing retractor 14 are also contemplated, including direct placement of retractor 14 through a tissue opening.

Retractor 14 includes a proximal coupling portion 34 adjacent proximal end 20. Proximal coupling portion 34 can include a ring portion 38 extending about proximal end 20 of retractor 14, and an extension portion 40. Link 16 can be coupled at connection 42 to extension portion 40 such that the light transmitted by link 16 is transmitted into proximal coupling portion 34 and dispersed about ring portion 38 and into body 18. Light is transmitted through body 18 toward distal end 22 to illuminate working space 26 and working channel 24. Connection 42 can be a threaded connection, luer connection, bayonet lock, snap fit, or other connection suitable for securing link 16 to proximal coupling portion 34. In the illustrated embodiment, extension portion 40 extends laterally from retractor body 18. Other embodiments contemplate extension portion 40 extends axially from body 18, or at an angle with body 18. Multiple extension portions are also contemplated.

Retractor 14 is shown as a cylindrical cannula with a circular cross-section. However, other retractor embodiments are contemplated. Other retractor examples are provided in U.S. patent application Ser. No. 09/815,693, filed Mar. 23, 2001; U.S. patent application Ser. No. 10/117,440, filed Apr. 25, 2002; and U.S. patent application Ser. No. 10/180,658, filed Jun. 26, 2002, each of which is incorporated herein by reference in its entirety. For example, retractor 14 can be provided with a body 18 that defines a working channel that is open along one or more sides thereof. Body 18 can be provided with a non-uniform cross-section along its length.

Link 16 is coupled to coupling portion 34 of retractor 14, where light transmitted by link 16 is dispersed around coupling portion 34. Coupling portion 34 is in communication with body 18 so that the light dispersed around coupling portion 34 can be transmitted to body 18 by material comprising retractor 14. The dispersed light can be transmitted with body 18 to distal end 22, where it is emitted into working channel 24 and distally of distal end 22 to illuminate the surgical space. Other embodiments contemplate that link 16 can be coupled to any portion of body 18 with a suitable connector. While link 16 is shown as being removable coupled with retractor 14, link 16 can also be integrally formed with or otherwise non-removably coupled with retractor 14.

Figure 2:
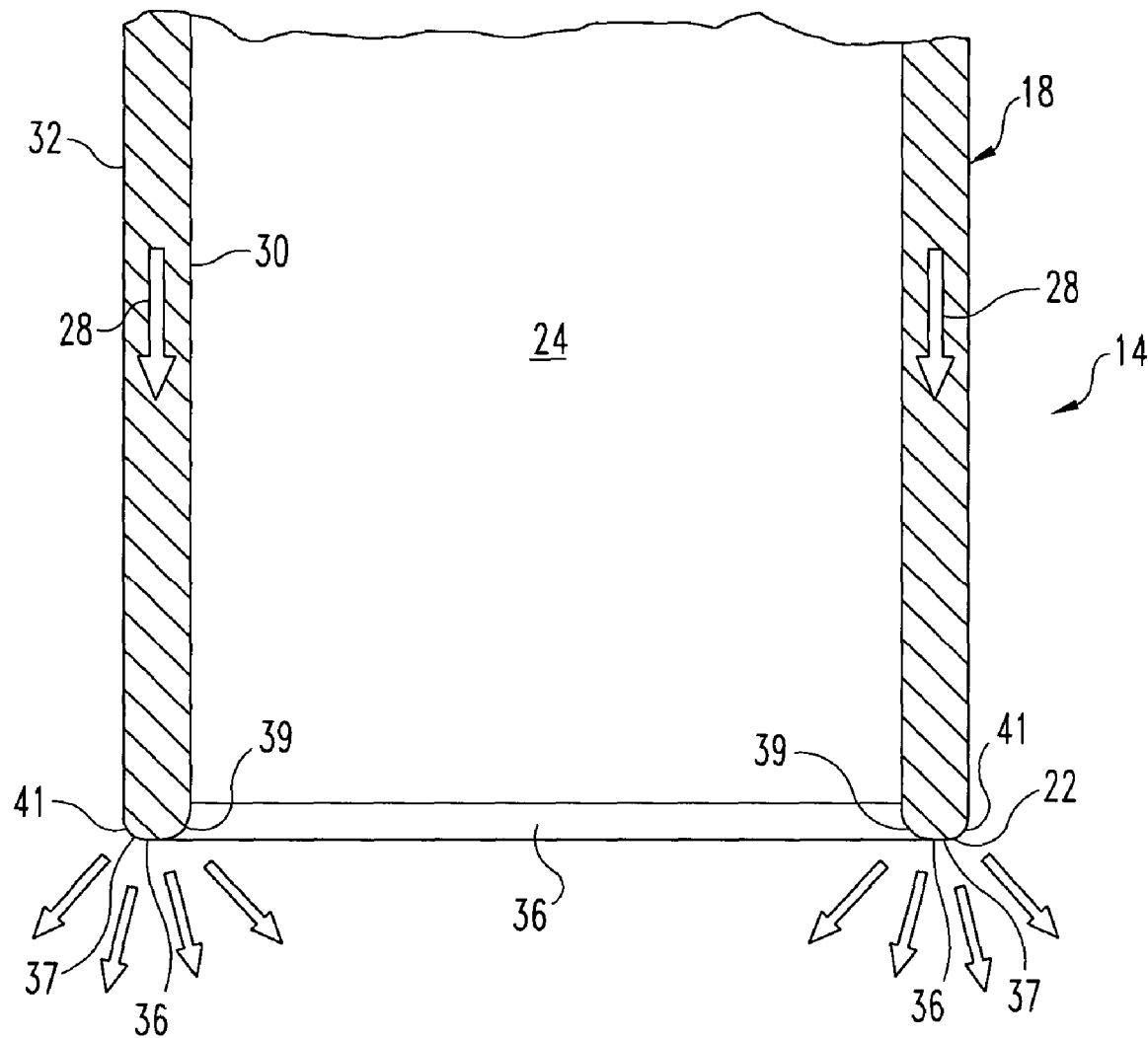
FIG. 2 is a sectional view along a portion of the distal end of the retractor of FIG. 1.

FIG. 2 provides a cross-section along a distal end portion of retractor 14. Body 18 of retractor 14 includes an inner wall surface 30 and an outer wall surface 32. Inner wall surface 30 can be concavely curved and extend around all or a portion of working channel 24. Light 28 can be dispersed around body 18 between inner wall surface 30 and outer wall surface 32. Light is transmitted through body 18 where it is emitted from emitting surface 36 adjacent distal end 22 to illuminate the surgical space. To facilitate transmission of light through retractor 14, it is contemplated that body 18 can be made from an internally reflective material. Examples of suitable material include glass, plastic, or any other material capable of transmitting light from proximal end portion 34 to distal end 22.

Emitting surface 36 can have a configuration that provides greater surface area for radiating light 28 about the surgical space by providing a discontinuity of inner wall surface adjacent distal end 22 to focus light toward working channel 24 and its extension beyond distal end 22. In the illustrated embodiment, emitting surface 36 is rounded toward working channel 24 to direct light toward the center of working channel 24. Other embodiments contemplate an emitting surface 36 that can be beveled, chamfered, or otherwise configured to increase the surface area adjacent distal end 22. It is further contemplated that light can be emitted from inner wall surface 30 to illuminate working channel 24 along all or a portion of the length of working channel 24.

In the illustrated embodiment, emitting surface 36 includes a first portion 37 extending from outer wall surface 32 toward inner wall surface 30. A second portion 39 extends from first portion 37 to inner walls surface 30. Second portion 39 is convexly curved toward working channel 24 and provides a rounded surface about which light can be emitted to illuminate the surgical space. First portion 37 is linear along at least a portion of distal end 22 to provide surface area for emission of light below the wall of body 18. A convexly curved third surface portion 41 provides surface area for emission of light in the working space outside the confines of working channel 24 to facilitate viewing of the surgical space and tissue in such locations. It may be desirable to view such tissue before performing surgical procedures thereon with instruments through working channel 24 or to reposition distal end 22 over such tissue.

Figure 3:
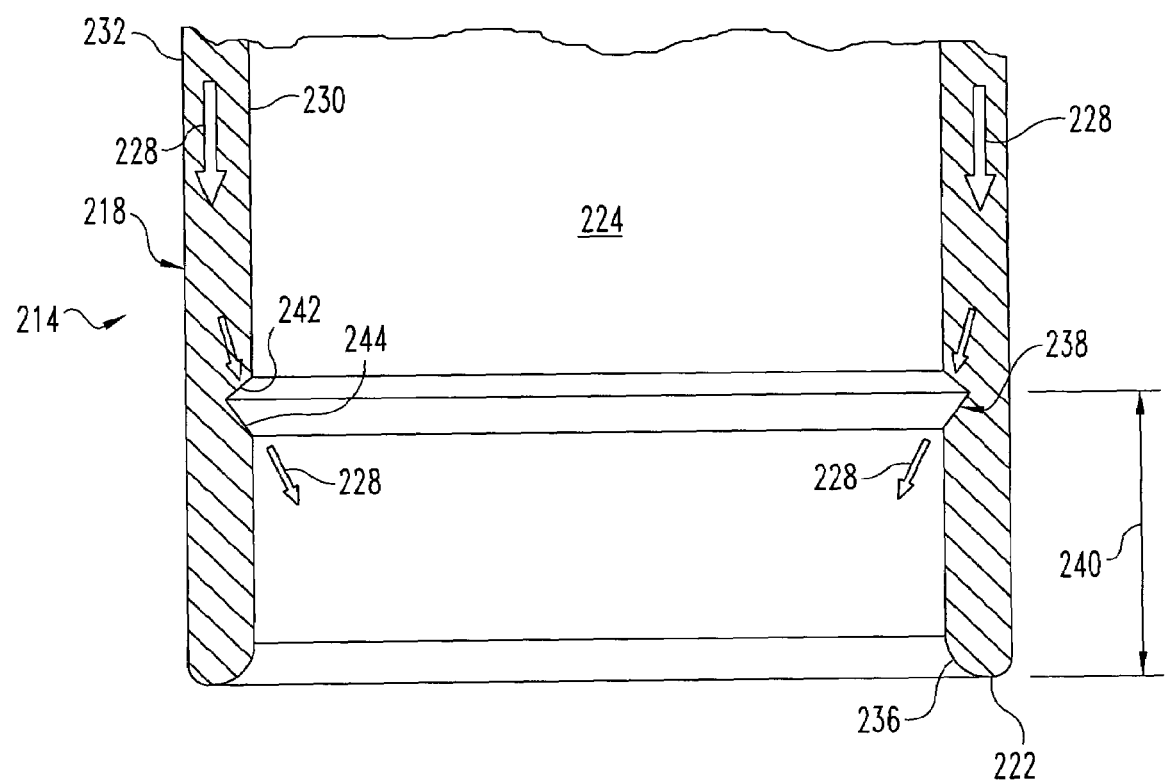
FIG. 3 is a sectional view along a portion of the distal end of another embodiment retractor.

FIG. 3 provides another embodiment retractor 214 that can be similarly attached to light source 12 with link 16. Retractor 214 includes a body 218 having an inner wall surface 230 and an outer wall surface 232 extending about working channel 224. Distal end 222 can be configured to provide an emitting surface 236 as discussed above with respect to emitting surface 36. Retractor 214 includes internal emitting surface 238 spaced from distal end 222 by distance 240. Emitting surface 238 provides a discontinuity in inner wall surface 230 that extends around at least a portion of body 218, including extending completely about working channel 224. In the illustrated embodiment, emitting surface 238 includes a proximal surface portion 242 and a distal surface portion 244 which form a V-shape extending from inner wall surface 230 into body 218 of retractor 214. Other embodiments contemplate multiple emitting surfaces 238 extending about all or a portion of working channel 224. Proximal surface portion 242 directs or reflects light 228 to focus light internally toward working channel 224. Accordingly, light is emitted into working channel 224 at a location proximally spaced from distal end 222. Other internal surface configurations are also contemplated, including one or more rounded channels or grooves in inner wall surface 230.

Figure 4:
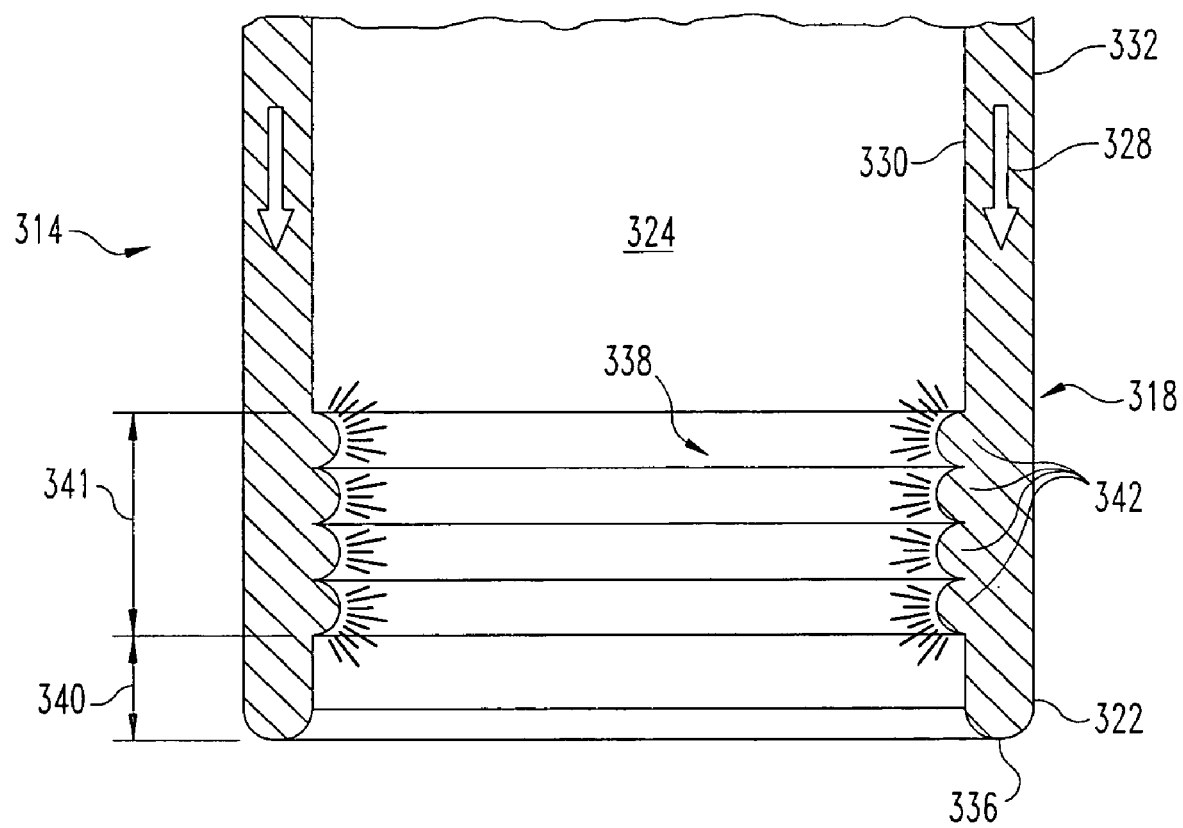
FIG. 4 is a sectional view along a portion of the distal end of another embodiment retractor.

FIG. 4 provides another embodiment retractor 314 that can be similarly attached to light source 12 with link 16. Retractor 314 includes a body 318 having an inner wall surface 330 and an outer wall surface 332 extending about working channel 324. Distal end 322 can be configured to provide an emitting surface 336 as discussed above with respect to emitting surface 36. Retractor 314 includes a discontinuity in inner wall surface 330 formed by internal emitting surface 338 spaced from distal end 322 by distance 340, and extending along inner wall surface 330 for a distance 341. In the illustrated embodiment, emitting surface 338 includes a number of protrusions 342 extending thereabout. In the illustrated embodiment, four protrusions 342 are provided adjacent one another, each of which include a semi-circular cross-sectional shape extending inwardly toward working channel 324 from inner wall surface 330. Other numbers of protrusions 342 are also contemplated, ranging from one protrusion to five or more protrusions. Other shapes for protrusions 342 are also contemplated, including V-shaped, semi-oval, rectangular, square, and polygonal cross-sectional shapes, for example. Protrusions 342 provide the light transmitting body 318 of retractor 314 with surface area in working channel 324 through which light 328 can be emitted and focused into working channel 324. Accordingly, greater illumination can be provided in working channel 324 at a location spaced from distal end 322.

Further embodiments contemplate masking the retractor to reduce or eliminate light emission from locations other than the space along the working channel and the working space adjacent the distal end of the retractor. For example, outer wall surfaces 32, 232, 332, and/or of retractors 14, 214, 314 could be masked to reduce or eliminate light emitting from these areas. Masking could extend along all of the length of the retractor body, or could be extended from the proximal end for a portion of the length such that a distal portion of body 18 is not masked, allowing light emission in the working space outside the confines of the retractor body.

Other embodiments contemplate a retractor having light transmitting elements in the body of the retractor, such as shown in FIG. 5. System 410 includes light source 12 coupled to a retractor 414 via link 16. Retractor 414 includes a body 418 defining a working channel or path 424 extending between and opening at proximal end 420 and distal end 422. Link 16 can be coupled to proximal end portion 434 in a direction that extends along the axis of the retractor. Retractor 414 includes a number of light transmitters 428 extending along body 418 between proximal end 420 and distal end 422. Light transmitters 428 can be fiber optic cable, light tubes, or other light transmitting element embeddable in the wall of body 418.

It is contemplated that light transmitters 428 can be radially dispersed, spaced or positioned about body 218 to provide light emission completely thereabout into the surgical space, including working channel 424 and working space 26. Light transmitters 428 can collect at connection 436 for coupling with link 16, and extend around proximal portion 434 to the desired locations through body portion 418. In one embodiment, light transmitters 428 are positioned in retractor 414 by over-molding retractor 414 around light transmitters 428. Other embodiments contemplate that passages are formed in retractor 414 and lights transmitters are placed in the formed passages.

Link 16 can include light transmitters 428 bundled therein for connection with light source 12 at the proximal or outer end of link 16. The distal end of link 16 can removably coupled or non-removably coupled with retractor 414 at or adjacent coupling portion 438. In the illustrated embodiment of FIG. 5, light transmitting elements extend axially along body 418 of retractor 414.

Other embodiments contemplate one or more light transmitting elements that extend transversely to body 418 to radially disperse light in working channel 424. For example in FIG. 6, one or more light transmitting elements 528 can extend circumferentially around working channel 424 in body 418. A linking light transmitting element 530 extends between light transmitting element 528 to deliver light thereto. In FIG. 7, one or more light transmitting elements 628 are spirally wound around working channel 424 in body 418.

While the invention has been illustrated and described in detail in the drawings and foregoing description, the same is to be considered as illustrative and not restrictive in character. All changes and modifications that come within the spirit of the invention are desired to be protected.

What is claimed is:

1. A retractor for illuminating a surgical space, comprising:
a body extending between a distal end and a proximal end and forming a tube defining a working channel for receiving at least one surgical instrument therethrough, said body comprised of light transmittable material, said body including a coupling portion for receiving light from a light source for transmission of light into said body, said body including a light emitting surface formed by a discontinuity in an inner wall surface of said body in communication with said working channel for reflection of light from said body into said working channel, said body further including an outer surface masked along at least a portion of a length of said body between said distal end proximal ends to prevent light from transmitting through said masked outer surface portion.

2. The retractor of claim 1, wherein said body includes a concavely curved surface defining said working channel.

3. The retractor of claim 1, wherein said light emitting surface includes a recess in said inner wall surface of said body adjacent said working channel.

4. The retractor of claim 3, wherein said body is tubular and said recess extends about said working channel.

5. The refractor of claim 4, wherein said light emitting surface is spaced proximally from said distal end of said body.

6. The retractor of claim 3, wherein said light emitting surface includes a proximal surface portion and a distal surface portion.

7. The refractor of claim 6, wherein said proximal and distal surface portions form a V-shape.

8. The retractor of claim 1, wherein said light emitting surface includes at least one protrusion extending transversely to a longitudinal axis of said body and into said working channel.

9. The refractor of claim 8, wherein said body is tubular and said inner wall surface extends around said working channel.

10. The retractor of claim 9, wherein said at least one protrusion forms a ring extending around said working channel.

11. The retractor of claim 10, wherein said at least one protrusion comprises a series of two or more protrusions adjacent one another.

12. The retractor of claim 8, wherein said at least one protrusion includes an outer surface convexly curved in a direction between said distal end and said proximal end of said body.

13. The retractor of claim 8, wherein said at least one protrusion is spaced a distance from said distal end.

14. The retractor of claim 1, wherein said light transmittable material is plastic.

15. The retractor of claim 1, wherein said coupling portion includes a ring portion extending about said proximal end of said body and an extension portion extending from said ring portion for coupling with said light source.

16. The refractor of claim 1, wherein said body includes an outer wall surface opposite said inner wall surface, said distal end and including a first surface portion extending from said outer wall surface toward said inner wall surface and a convexly curved second surface portion extending from said first portion to said inner wall surface.

17. The retractor of claim 16, wherein said body is tubular and said working channel is enclosed by said inner wall surface.

18. The retractor of claim 17, wherein said first surface portion is orthogonally oriented relative to said outer wall surface.

19. A retractor for illuminating a surgical space, comprising:
a tubular body extending between a distal end and a proximal end, said body including an inner wall surface defining a working channel for receiving at least one surgical instrument therethrough, said body comprised of light transmittable material and including a light emitting surface on said inner wall surface in communication with said worlcing channel, said light emitting surface being spaced a distance from said distal end to focus light from said body into said working channel, said body further including an outer wall surface masked along at least a portion of a length of said body between said distal end proximal ends to prevent light from transmitting through said masked outer surface portion.

20. The retractor of claim 19, wherein said working channel includes a circular shape cross-section transversely to a longitudinal axis of said body.

21. The retractor of claim 19, wherein said light emitting surface includes a recess in said inner wall surface.

22. The refractor of claim 21, wherein said light emitting surface includes a proximal surface portion and a distal surface portion.

23. The retractor of claim 22, wherein said proximal and distal surface portions form a V-shape.

24. The refractor of claim 21, wherein said recess is orthogonally oriented relative to a longitudinal axis of said body.

25. The refractor of claim 24, wherein said recess extends completely about said worldng channel.

26. The refractor of claim 19, wherein said light emitting surface includes at least one protrusion extending from said inner surface into said working channel.

27. The retractor of claim 26, wherein said at least one protrusion extends around said working channel.

28. The retractor of claim 26, wherein said at least one protrusion comprises a series of two or more protrusions adjacent one another and extending about said working channel and spaced along said inner wall surface of said body.

29. The retractor of claim 26, wherein said at least one protrusion includes an outer surface convexly curved in the direction between said distal end and said proximal end of said body.

30. The retractor of claim 19, wherein said body comprises a proximal coupling portion including a ring portion extending about said proximal end of said body and an extension portion extending from said ring portion for coupling with a light source.

31. The refractor of claim 19, wherein said body includes the outer wall surface, said distal end including a first surface portion extending from said outer surface toward said inner surface and a convexly curved second surface portion extending from said first portion to said inner wall surface.

32. The retractor of claim 31, wherein said first surface portion is orthogonally oriented to said outer surface.

33. A retractor for illuminating a surgical space, comprising:
a tubular body extending between a distal end and a proximal end, said body including an inner wall surface defining a working channel for receiving at least one surgical instrument therethrough, said body comprised of light transmittable material and including at least one light transmitter in a wall of said body to transmit light along said body and into said working channel, wherein said at least one light transmitter extends circumferentially about at least a proximal portion of said tubular body.

34. The refractor of claim 33, wherein said at least one light transmitter includes a plurality of light transmitters radially spaced about and axially extending along said tubular body.

35. The retractor of claim 33, wherein said at least one light transmitter extends circumferentially about said tubular body between said distal end and said proximal end.

36. The retractor of claim 33, wherein said at least one light transmitter extends spirally about said tubular body.

37. The retractor of claim 33, wherein said at least one light transmitter is an optical fiber.

38. A system for illuminating a surgical space, comprising:
a retractor comprised of light transmittable material, said retractor extending between a distal end and a proximal end and defining a working channel for receiving at least one surgical instrument therethrougb and a proximal coupling portion that extends around said working channel at said proximal end, said retractor further including an inner wall surface extending about said working channel and a discontinuity in said inner wall surface to direct light into said working channel;
a light source operable to generate light; and
a link coupling said light source to said coupling portion of said retractor to deliver light around said coupling portion for transmission of light from said coupling portion through said retractor and into said working channel.

39. The system of claim 38, wherein said light transmitting material is plastic.

40. The system of claim 38, wherein said body includes an outer surface masked along at least a portion thereof to prevent light transmission through said outer surface.

41. The system of claim 38, wherein said proximal coupling portion includes a ring portion extending about said proximal end of said body and an extension portion extending from said ring portion for coupling with said light source.

42. The system of claim 38, wherein said link includes a plurality of optical fibers.

* * * * *